US008497098B2

(12) United States Patent
Eppelmann et al.

(10) Patent No.: US 8,497,098 B2
(45) Date of Patent: Jul. 30, 2013

(54) BIOCHEMICAL SYNTHESIS OF 1,4-BUTANEDIAMINE

(75) Inventors: Katrin Eppelmann, Kalamazoo, MI (US); Petrus M. M. Nossin, Nederweert (NL); Leon J. R. M. Raeven, Sittard (NL); Susanne M. Kremer, Linnich-Gereonsweiler (DE); Marcel G. Wubbolts, Sittard (NL)

(73) Assignee: DSM IP Assets B.V., Heerlen (NL)

( * ) Notice: Subject to any disclaimer, the term of this patent is extended or adjusted under 35 U.S.C. 154(b) by 1257 days.

(21) Appl. No.: 11/632,458

(22) PCT Filed: Jul. 11, 2005

(86) PCT No.: PCT/EP2005/007606
§ 371 (c)(1),
(2), (4) Date: Jun. 29, 2007

(87) PCT Pub. No.: WO2006/005603
PCT Pub. Date: Jan. 19, 2006

(65) Prior Publication Data
US 2009/0011478 A1    Jan. 8, 2009

(30) Foreign Application Priority Data

Jul. 15, 2004   (EP) .................................... 04077046

(51) Int. Cl.
*C12P 13/00*    (2006.01)
*C12N 9/00*    (2006.01)
*C12N 1/20*    (2006.01)
*C12N 15/00*    (2006.01)
*C07H 21/04*    (2006.01)

(52) U.S. Cl.
USPC ..... 435/128; 435/183; 435/252.3; 435/320.1; 536/23.2

(58) Field of Classification Search
None
See application file for complete search history.

(56) References Cited

FOREIGN PATENT DOCUMENTS

| EP | 0 726 240 | 8/1996 |
|---|---|---|
| EP | 1 260 588 | 11/2002 |
| WO | 01/11062 | 2/2001 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
International Search Report for PCT/EP2005/007606 mailed Oct. 7, 2005.
Kashiwagi et al. Adjustment of polyamine contents in *Escherichia coli* Journal of Bacteriology, vol. 170, No. 7, pp. 3131-3135, Jul. 1988.
Macrae et al. "Complementation of a polyamine-deficient *Escherichia coli* mutant by expression of mouse ornithine decarboxylase" Molecular and Cellular Biology, vol. 7, No. 1, pp. 564-567, Jan. 1987.
Rajagopal et al. "Use of inducible feedback-resistant N-acetylglutamate synthetase (argA) genes for enhanced arginine biosynthesis by genetically engineered *Escherichia coli* K-12 strains" Applied and Environmental Microbiology, vol. 64, No. 5, pp. 1805-1811, May 1998.
Sakanyan et al. "Genes and enzymes of the acetyl cycle of arginine biosynthesis in *Corynebacterium glutamicum*: Enzyme evolution in the early steps of the arginine pathway" Microbiology, vol. 142, pp. 99-108, Jan. 1996.
Nakada et al. "Identification of the putrescine biosynthetic genes in *Pseudomonas aeruginosa* and characterization of agmatine deiminase and N-carbamoylputrescine amidohydrolase of the arginine decarboxylase pathway" Microbiology, vol. 149, No. 3, pp. 707-714, Mar. 2003.
Cunin et al. "Biosynthesis and metabolism of arginine in bacteria" Microbiological Reviews, vol. 50, No. 3, pp. 314-352, Sep. 1986.
Tabor et al. "Polyamines in microorganisms" Microbiological Reviews, vol. 49, No. 1, pp. 81-99, Mar. 1985.
Cohen *A Guide to the Polyamines*, Oxford University Press, pp. 122-183, 1998.
Boyle et al. "Expression of the cloned gene encoding the putrescine biosynthetic enzymes and methionine adenosyltransferase in *Escherichia coli* (speA, speB, speC and metK)" Gene, vol. 30, No. 1-3, pp. 129-136, Oct. 1984.
Klein et al. "Reconstitution of a bacterial/plant polyamine biosynthesis pathway in *Saccharomyces cerevisiae*" Microbiology, vol. 145, No. 2, 301-307, Feb. 1999.
Fukuchi et al. Decrease in cell viability due to the accumulation of spermidine in spermidine acetyltransferase-deficient mutant of *Escherichia coli*Journal of Biological Chemistry, vol. 270, No. 32, pp. 18831-18835, Aug. 11, 1995.
Suzuki et al. "Antizyme protects against abnormal accumulation and toxicity of polyamines in ornithine decarboxylase-overproducing cells" Proc. Natl. Acad. Sci. USA, vol. 91, No. 19, pp. 8930-8934, Sep. 1994.

* cited by examiner

*Primary Examiner* — Christian Fronda
(74) *Attorney, Agent, or Firm* — Nixon & Vanderhye P.C.

(57) ABSTRACT

The invention relates to a process for biochemical synthesis of 1,4-butanediamine in a microorganism having an increased level of an ornithine decarboxylase activity (increased ODC activity) as compared to the native level of the ornithine decarboxylase activity, wherein in the microorganism also an increased activity of N-acetylglutamate formation is present as compared to the native level of activity of N-acetylglutamate formation in the microorganism and wherein 1,4-butanediamine produced in the microorganism is excreted into a fermentation broth, and is recovered from the fermentation broth. The invention also relates to vectors, plasmids and hosts carrying a corresponding increased ODC activity and an increased activity of N-acetylglutamate formation.

19 Claims, No Drawings

US 8,497,098 B2

BIOCHEMICAL SYNTHESIS OF 1,4-BUTANEDIAMINE

This application is a U.S. national stage of International Patent Application No. PCT/EP2005/007606, filed 11 Jul. 2005, which designated the U.S. and claims priority of EP 04077046.3, filed 15 Jul. 2004; the entire contents of each of which are hereby incorporated by reference.

The present invention relates to a new process for biochemical synthesis of 1,4-butanediamine (CAS number 110-60-1; a compound also referred to as tetramethylenediamine; in biochemical literature it is also being referred to as putrescine) in a microorganism having an increased level of an ornithine decarboxylase activity as compared to the native level of the ornithine decarboxylase activity. Ornithine decarboxylase hereinafter also will be referred to as ODC. Generally such microorganisms having ODC activity are known to be capable of producing polyamines such as spermidine and spermine, which are the common names for respectively the products N-(3-aminopropyl)-1,4-butanediamine and N,N'-bis-(3-aminopropyl)-1,4-butanediamine. Such compounds, as well as various short linear diamines themselves such as, for instance, 1,4-butanediamine and 1,5-pentanediamine (also referred to as cadaverine), are often referred to in biochemical studies as polyamines, even though from a strictly chemical definition of polyamines a higher number of amino groups would be expected. For the purposes of the present patent application, however, the term polyamines is being used in its biochemical meaning and therefore includes 1,4-butanediamine.

The compound 1,4-butanediamine is an important raw material for the production of some of the major engineering plastics: polyamide-4,6, either in the form of a homopolymer, or copolymerised, for example, with about 5 wt. % of polyamide-6 monomer (caprolactam). The homopolymer polyamide-4,6 (nylon-4,6) was described as early as 1938 (U.S. Pat. No. 2,130,948, Carothers). It is the polycondensation product of the monomers 1,4-butanediamine and adipic acid. Presently, especially compounds of polyamide-4,6 are being produced and sold by DSM in the Netherlands under the trade name STANYL®.

For the synthesis of 1,4-butanediamine a number of chemical routes are known. All these chemical routes suffer from the disadvantage that starting materials have to be obtained form sources that are considered to be non-renewable. There exists, however, a substantial need for providing new and feasible routes for the synthesis of 1,4-butanediamine starting from renewable carbon sources and using biochemical processes (also referred to as "biotransformation") in living cells. In general, polyamines are considered to be toxic for any cell or microorganism used in biochemical oduction. Therefore, until now such new routes by biochemical synthesis, however, were believed to be unattractive.

This can for instance be seen from the following references: Fukuchi et al., J. Biol. Chem., Vol. 270 (1995), pages 18831-18835; and Suzuki et al., Proc. Natl. Acad. Sci. USA, Vol. 91 (1994), pages 8930-8934.

Fukuchi clearly describes the decrease in cell viability (and of synthesis of almost all kinds of proteins) due to the accumulation of spermidine in spermidine acetyltransferase-deficient cells of E. coli (i.e. in cells lacking the acetyltransferase SpeG). It is to be noticed that Limsuwum et al. (J. Bacteriol. Vol. 182 (2000), pages 5373-5380) have shown that at low temperatures such problems can be overcome by overexpression of the dedicated gene speG. Spermidine is a product that is being produced in cells from 1,4-butanediamine as an intermediate. Accordingly, biosynthesis of 1,4-butanediamine inevitably also leads to formation of spermidine.

Suzuki et al. on the one hand also demonstrate (in mice cells), that overexpression of ODC results in accumulation of polyamines, especially of spermidine, and that—upon addition of small amounts of spermidine—already cell death is observed even in cells that are not deficient in speG. Suzuki et al. suggest that this lowered cell viability is due to an insufficient feedback inhibition of ODC by antizymes and can be overcome by overproduction of a suitable antizyme. Such overproduction of antizymes then also would lower the production of polyamines in the cells and is therefore not feasible for DAB production.

Further, as Kashiwagi et al. described in J. Bacteriol. Vol. 170 (1988), pages 3131-3135, the contents of polyamines in E. coli can be adjusted by overexpression of an ornithine decarboxylase (ODC) encoding gene, in particular of the constitutively expressed speC. For their experiments the plasmid pODC as produced by Boyle et al. (Methods in Enzymology, Vol. 94 (1983), pages 117-121, was used in the cloning. Clearly, such overproduction of ornithine decarboxylase did not lead to strongly increased levels of 1,4-butanediamine content in the cells. At a 70-fold level of ODC no more than a 20% increase of 1,4-butanediamine content in the cells was observed, independent of the amount of ornithine added to the cells. On the other hand, however, cells grown in the presence of ornithine were shown to exhibit increased excretion of 1,4-butanediamine. At the 70-fold level of ODC in total about 8,5 times higher production of 1,4-butanediamine (the titer of 1,4-butanediamine produced was approximately 20-25 mg/l, in total for in- and external concentrations, i.e. an extremely low concentration) was found. The authors suggested that such rather low efficiency of 1,4-butanediamine production might be due to shortage of ornithine, and tried to solve this by external feeding of ornithine, but only reached a minor improvement. Accordingly, it would seem to be impossible to provide biochemical synthesis processes for the production of 1,4-butanediamine at significantly higher levels than 30 mg/l.

These studies mentioned above, moreover, were not directed to synthesis of polyamines (including 1,4-butanediamine) as such, but rather tried to get more insights in the physiological functions of polyamines at the molecular level. At higher levels of ornithine in the cells presumably also more arginine would be present in the cells. According to the teaching of Kashiwagi, such higher amounts of arginine should have a substantial negative effect on 1,4-butanediamine formation.

EP-A-0726240 until now is one of the very few patent references relating to the biochemical synthesis of polyamines, including 1,4-butanediamine. However, it describes the production of, inter alia, 1,4-butanediamine by fermentation of natural products containing proteins as a major component. In said process, the natural products are first treated by subjecting them to partial or total degradation, and any undesirable compounds (e.g. Hg, Cr, As, Cd, Se and Pb), cell growth inhibitors, pesticides, antibiotics, detergents, soaps, fats, oils, cyanides and phenols are then removed before the fermentation step. The putrescine and other diamines produced in such a way are being (re-)used as fertilizers and manures, but contain such large number of other substances that they are unsuitable as a raw material for the production of, for example, polyamide-4,6.

Accordingly, there remains a need for an efficient alternative biosynthetic route for the synthesis of 1,4-butanediamine at significantly higher titers than about 30 mg/l, preferably even without the need for external feeding of (expensive)

ornithine. This need for improved availability of 1,4-diaminobutane is based on its intended use as a starting material, for instance, for the production of polyamide-4,6. In general, the routes to 1,4-butanediamine as are known until today are quite laborious and troublesome, and may lead to a quality of said product which—without further purification—is difficult to be used in the production of nylons. The known chemical routes to 1,4-butanediamine require relatively expensive starting materials and reactants (including reactants that are difficult to handle), and relatively severe reaction conditions of temperature and pressure in a multi-step and multi-reactor design, as well as the use of expensive catalyst systems. Accordingly there remains a need for alternative routes to 1,4-butanediamine, preferably from much less expensive raw materials and avoiding problems of handling reactants like hydrocyanic acid. It is well known that naturally growing, and thus renewable, materials from agricultural production are the basis for carbon sources such as glucose (or other appropriate carbon sources and mixtures thereof that can be used in fermentation. Such renewable materials are relatively cheap and abundantly available. In general, it is considered to be very advantageous if renewable materials can be used as starting materials for all kinds of chemical materials.

It is thus an aim of the present invention to provide improved possibilities for large-scale industrial production of 1,4-butanediamine by biotransformation.

The present inventors surprisingly have found that this aim is achieved with a new process for biochemical synthesis of 1,4-butanediamine in a microorganism having an increased level of an ornithine decarboxylase activity (increased ODC activity) as compared to the native level of ornithine decarboxylase activity, wherein in the microorganism also an increased activity of N-acetylglutamate formation is present as compared to the native level of activity of N-acetylglutamate formation in the microorganism and that 1,4-butanediamine produced in the microorganism is excreted into a fermentation broth, and is recovered from the fermentation broth.

As meant in the present patent application, the term "biochemical synthesis" (a term that, in the context of this patent application, alternatively is referred to as "biotransformation") includes not only processes which involve—besides a number of purely chemical reaction steps—one or more biocatalytic reactions using whole cells of suitable production strains, but also purely biochemical processes using whole cells of suitable production strains. Such purely biochemical processes, respectively, are referred to as fermentations in case the biochemical synthesis starts from a suitable carbon source, or are referred to as precursor fermentations in case the biosynthesis starts from an intermediate product already having a carbon skeleton from which the target molecule to be synthesized can be obtained. The processes may be carried out either under aerobic or under anaerobic conditions.

The biocatalytic reactions in the biochemical synthesis of the present invention can be carried out either in vivo or in vitro. Generally, in vivo processes are processes carried out when using living cells (the term "living cells" thereby also including so-called resting cells); in vitro processes, on the other hand, usually are being carried out using cell lysates or (partly) purified enzymes. The biochemical synthesis according to the present invention is carried out in a microorganism. This can be done using whole cells of suitable production strains, but also may be carried out using permeabilized cells; the differentiation between in vivo and in vitro, however, does not make much sense for processes being carried out with permeabilized cells or immobilized host cells. It will be evident, however, that individual biocatalytic steps from the process of the invention, when carried out, for instance, by using, immobilized enzymes, etc. are considered equivalent to such steps in the biochemical synthesis as meant in the context of the present application.

Ornithine decarboxylases (i.e. enzymes having ornithine decarboxylation activity, or ODCs) are enzymes classified in class E.C. 4.1.1.17. The level of activity of an ornithine decarboxylase, if overproduced, can easily be compared with the native (i.e. non-overproduced) level of ornithine decarboxylase activity under standard conditions (at 37° C. in the presence of ornithine and PLP) within cell free extracts using the Sigma Diagnostics carbon dioxide detection kit (Sigma); assay described in Osterman, A. L. et al. 1994, Biochemistry 33, p. 13662-13667. The skilled man, accordingly, can easily establish whether the ODC used has an increased level of ornithine decarboxylase activity (increases ODC activity) as compared to the native level of the ornithine decarboxylase activity in the microorganism used by determination of the protein content, or by determining the RNA level. Various standard procedures for determination of protein content, for instance colorimetric as well as spectroscopic methods, are described in Lottspeich and Zorbas, Bioanalytik, Spektrum Akademischer Verlag GmbH, Heidelberg/Berlin, ISBN 3-8274-0041-4 (1998), Chapters 3, 5, 21, 22 and 24. Methods for determination of protein level as well as RNA level, for instance northern hybridization, RT-PCR, and many other methods, are described in J. Sambrook, E. F. Fritsch and T. Maniatis, Molecular Cloning, A Laboratory Manual, $2^{nd}$ Edition, Cold Spring Harbor Laboratory Press, ISBN 0-87969-309-6 (1989). Many other standard procedures, however, are known to the skilled man in this analytic field and do not need to be mentioned here.

Suitable ornithine decarboxylases that can be used in the process of the invention, are all enzymes and mutants thereof, that are capable of decarboxylating ornithine. Any such enzyme may be used in the process of the invention, at an increased level of activity, i.e. in overproduced form. Such increased level of activity can be achieved by any means known to the skilled man, for instance by means of increasing the gene copy number, or by increasing the endogenous activity or structure of the enzymes by means of mutations, or by using deregulated enzymes. However, and most preferably, it also can be achieved by means of overexpressing an ornithine decarboxylase gene with increased transcriptional and/or translational efficiency. In addition it is to be noticed, that the term "increased level of activity" as used herein for any specifically named enzyme activity is also intended to encompass such situations where the activity of such enzyme activity, for instance an ornithine decarboxylase, is not present at all in the natural source of the microorganism wherein the reaction is taking place, but is introduced therein purposively by genetic modification.

In the process according to the invention, an increased level of activity of N-acetylglutamate formation (as further defined hereinbelow, when the discussion of the pertaining dependent claims is presented) needs to be present as compared to the native level of activity of N-acetylglutamate formation in the microorganism. Comparison of the increased and native activity levels of N-acetylglutamate formation can easily be done, similar to such determination for the ODCs, with appropriate test reactions under standard conditions (assay described in Abadjieva, A., 2001, J. Biol. Chem., 276, p. 42869-42880) within cell free extracts by a radioassay using L-[$^{14}$C]glutamate and acetyl-CoA as substrates.

1,4-Butanediamine is, according to the present invention, produced in the microorganism with increased ODC and N-acetylglutamate formation activity by biotransformation, and is excreted into the fermentation broth surrounding the microorganism. The 1,4-butanediamine is excreted into and recovered from the fermentation broth.

According to the present invention, thus, an improved biochemical process for the synthesis of 1,4-butanediamine is provided, and the resulting 1,4-butanediamine is excellently suitable as raw material, for instance, for the production of polyamide-4,6.

The formation of 1,4-butanediamine in the high amounts as produced according to the invention is most surprising, because of the fact that an increased level of ODC activity (together with the increased activity of formation of N-acetylglutamate), without any additional measures being taken for avoiding the negative effects of polyamine formation on the viability of the cells, would be expected to result in death of cells.

As mentioned above, any ODC enzyme may be used, at an increased level of activity, i.e. in overproduced form, in the process of the invention.

According to the present invention all ornithine decarboxylases can be used that have sufficient, i.e. at least 30%, more preferably at least 45%, and most preferably at least 65% identity with the ODC from the *E. coli* reference enzyme, and are capable of catalyzing the ornithine decarboxylation reaction. Many ODCs are known having such relatively high level of identity with the *E. Coli* reference enzyme.

Determining identity percentages with reference enzymes can be performed by methods known to the skilled man, for instance by using the protein sequence of the reference enzyme as a "query sequence" to perform a search against public databases to, for example, identify other family members or related sequences. Such searches can be performed using BLAST programs (version 2.2) using the default parameters of respective program. See http://www.ncbi.nlm.nih.gov.

Preferably, the increased ODC activity is achieved by overexpression of an ornithine decarboxylase encoding gene speF or speC (each belonging to E.C. 4.1.1.17) originating from one of the genera selected from the group consisting of *Escherichia, Shigella, Salmonella, Yersinia*, and *Shewanella*. The ornithine decarboxylase speF is an inducible ornithine decarboxylase; ornithine decarboxylase speC is a constitutive ornithine decarboxylase.

More preferably, the ornithine decarboxylase encoding gene is originating from one of the species selected from the group consisting of *Escherichia coli, Shigella flexneri, Salmonella typhimutium, Yersinia pestis*, and *Shewanella oneidensis*. Until now speC has been investigated in literature much more than speF. Most surprisingly, however, and most preferably, best results according to the present invention are achieved when the ornithine decarboxylase encoding gene is speF, more particularly speF originating from one of the species selected from the group consisting of *Escherichia coli, Salmonella typhimutium*, and *Shewanella oneidensis*. When compared to results with overexpression of the constitutive speC ornithine decarboxylase encoding gene, by far the best results according to the present invention indeed are being achieved when using speF.

In the context of the present application, any gene being homologous with any of the abovementioned ornithine decarboxylases and coding for enzymes having ornithine decarboxylase activity sufficiently comparable to the ornithine decarboxylases shown, is suitable in the process of the invention. Such equivalent genes can suitably be obtained by means of any appropriate cloning strategy known to the skilled man, for instance, by the methods described in the experimental part hereof. Alternatively, such equivalent ornithine decarboxylase genes can also be obtained by purposive construction.

The term activity of N-acetylglutamate formation represents, in the context of the present patent application, any enzyme activity, whether due to a single enzyme or a combination of enzymes, capable of leading to intracellular formation of N-acetylglutamate.

According to the present invention, in particular, all N-acetylglutamate synthases can be used that have sufficient, i.e. at least 30%, more preferably at least 45%, even more preferably at least 60%, and most preferably at least 75% identity with the N-acetylglutamate synthase from the *E. coli* reference enzyme, and are capable of catalyzing the N-acetylglutamate formation reaction. Many N-acetylglutamate synthases are known having such relatively high level of identity with the *E coli* reference enzyme.

Preferably, increased activity of N-acetylglutamate formation is achieved by overexpression of either an N-acetylglutamate synthase encoding gene argA (belonging to E.C. 2.3.1.1) and/or an $N^2$-acetyl-L-ornithine: L-glutamate N-acetyl transferase encoding gene argJ (belonging to E.C. 2.3.1.35). It will be evident, that any gene coding for an enzyme or mutant thereof having the same functionality of one of the enzymes as mentioned here, will be considered to be equivalent with such enzyme in one of the classes E.C. 2.3.1.1 or 2.3.1.35.

In one of the preferred embodiments of the present invention, the increased activity of N-acetylglutamate formation is achieved by overexpression of an N-acetylglutamate synthase encoding gene argA (belonging to E.C. 2.3.1.1) originating from one of the genera selected from the group consisting of *Escherichia, Shigella, Salmonella, Yersinia, Photorhabdus*, and *Buchnera*. These ArgA enzymes require the presence of (or supply of) co-enzyme A for being active in their N-acetylglutamate formation.

In this embodiment the increased activity of N-acetylglutamate formation is achieved by overexpression of an N-acetylglutamate synthase encoding gene argA originating from one of the species selected from the group consisting of *Escherichia coli, Shigella flexneri, Salmonella enterica, Yersinia pestis, Photorhabdus luminescens*, and *Buchnera aphidicola*.

In another preferred embodiment of the present invention, the increased activity of N-acetylglutamate formation is achieved by overexpression of an $N^2$-acetyl-L-ornithine:L-glutamate N-acetyl transferase encoding gene argJ (belonging to E.C. 2.3.1.35) originating from one of the genera selected from the group consisting of *Bacillus, Listeria, Oceanobacillus, Staphylococcus, Lactobacillus, Corynebacterium, Mycobacterium, Thermobifida, Streptomyces*, and *Bifidobacterium*.

Suitable $N^2$-acetyl-L-ornithine: L-glutamate N-acetyl transferases that can be used in the process according to the invention are $N^2$-acetyl-L-ornithine:L-glutamate N-acetyl transferases that have sufficient, i.e. at least 20%, more preferably at least 30%, and most preferably at least 40% identity with the $N^2$-acetyl-L-ornithine:L-glutamate N-acetyl transferase from the *Bacillus* reference species, and are capable of catalyzing the $N^2$-acetyl-L-ornithine:L-glutamate N-acetyl transfer reaction. Many the $N^2$-acetyl-L-ornithine:L-glutamate N-acetyl transferases are known having such level of identity with the corresponding *Bacillus* reference enzyme.

Contrary to the ArgA enzymes, the ArgJ enzymes do not require any presence of (or supply of) co-enzyme A for being active in their N-acetylglutamate formation. Accordingly, these ArgJ enzymes are clearly preferred above the ArgA enzymes for use in industrial applications.

In this other preferred embodiment of the present invention, the increased activity of N-acetylglutamate formation is achieved by overexpression of an $N^2$-acetyl-L-ornithine:L-glutamate N-acetyl transferase encoding gene argj originating from one of the species selected from the group consisting of *Bacillus cereus, Listeria monocytogenes, Oceanobacmlus iheyensis, Staphylococcus epidermis, Lactobacillus plantarum, Lactobacillus lactis, Corynebacterium glutamicum, Mycobacterium leprae, Thermobifida fusca, Streptomyces coelicor*, and *Bifidobacterium longum*.

In the context of the present application, any gene being homologous with any of the abovementioned N-acetylglutamate formation activity and coding for enzymes having N-acetylglutamate formation activity sufficiently comparable to the N-acetylglutamate formation enzymes shown, is suitable in the process of the invention. Such equivalent genes can suitably be obtained by means of any suitable cloning strategy known to the skilled man, for instance, by the methods described in the experimental part hereof. Alternatively, such equivalent N-acetylglutamate formation genes can also be obtained by purposive construction.

In a further preferred embodiment of the present invention, the process for the biochemical synthesis of 1,4-butanediamine is carried out in a microorganism wherein, additionally, also an increased enzyme activity is obtained for at least two other enzymes by means of overexpression of either
(i) an arginine decarboxylase encoding gene speA (belonging to E.C. 4.1.1.19) and an agmatinase encoding gene speB (belonging to E.C. 3.5.3.11; also referred to as agmatine ureahydrolase encoding gene); or
(ii) an arginine decarboxylase encoding gene speA (belonging to E.C. 4.1.1.19), and an agmatine iminohydrolase encoding gene aguA (belonging to E.C. 3.5.3.12; also referred to as agmatine deiminase encoding gene), and an N-carbamoylputrescine amidohydrolase encoding gene aguB (belonging to E.C. 3.5.1.53), and optionally also an agmatinase encoding gene speB (belonging to E.C. 3.5.3.11).

The advantage of this further preferred embodiment is that 1,4-diaminobutane is formed in even higher amounts.

Overexpression as meant herein, can be achieved by any method known to the skilled man; for instance by increasing the translational and/or transcriptional efficiency of the respective gene, but also by any other known methods such as increasing the gene copy number, or by increasing the endogenous activity or structure of the enzymes by means of mutations, or by using deregulated enzymes. As meant in part (i) of the further preferred embodiment mentioned here above hereof the combination of SpeA and SpeB is intended to represent any functional combination (whether in a combined fusion protein, or as separate enzyme activities) of SpeA and SpeB. In fact, this combination also might be designated as SpeAB. Part (ii) hereof represents, that in such combinations of SpeA and SpeB, the SpeB-part itself may be replaced by any functional combination (whether in a combined fusion protein, or as separate enzyme activities) of AguA and AguB.

Janowitz et al., FEBS Letters 544 (2003), 258-261, have described that agmatine deiminase AguA is involved in the arginine decarboxylase pathway in higher plants. It is further known from Nakada et al., Microbiology, 149 (2003), 707-714, that the conversions catalyzed by SpeB also can be catalyzed by enzymes occurring in plants, namely by the combined action of agmatine deiminase AguA and N-carbamoyl-putrescine amidohydrolase AguB. Accordingly, instead of, or even in combination with, SpeB in the context of the present invention also AguA and AguB can be used.

Sources for such aguA and aguB genes could be *Arabidopsis thaliana* and *Lycopersicon esculentum*, but comparable genes can be found in mutants of *Pseudomonas aeroginosa*.

In the context of the present application, any gene being homologous with any of the abovementioned arginine decarboxylases, respectively agmatinases, or agmatine iminohydrolases or N-carbamoylputrescine amidohydrolases, and coding for such respective enzymes having arginine decarboxylase (respectively agmatinase, or agmatine iminohydrolase or N-carbamoylputrescine amidohydrolase) activity sufficiently comparable to the respective enzymes—as the case may be—is suitable in this further preferred embodiment of the process of the invention. Such equivalent genes suitably can be obtained by means of any suitable cloning strategy known to the skilled man, for instance, by the methods described in the experimental part hereof. Alternatively, such equivalent genes also can be obtained by purposive construction.

Accordingly, in this preferred embodiment of the process of the present invention, also additional combinations of overexpressed genes are being used, namely genes encoding for (i) arginine decarboxylase and agmatinase, or (ii) arginine decarboxylase and agmatine iminohydrolase and N-carbamoylputrescine amidohydrolase, and optionally agmatinase.

In this preferred embodiment of the process according to the present invention, in particular, all arginine decarboxylases can be used that have sufficient, i.e. at least 30%, more preferably at least 45% identity, and most preferably at least 65% identity with the arginine decarboxylase from the *E. coli* reference enzyme, and are capable of catalyzing the arginine decarboxylation reaction. Many arginine decarboxylases are known having such relatively high level of identity with the *E. coli* reference enzyme.

Moreover, in said embodiment, in particular all agmatinases can be used that have sufficient, i.e. at least 30%, more preferably at least 45%, and most preferably at least 60% identity with the agmatinase from the *E. coli* reference enzyme, and are capable of catalyzing the agmatinase reaction. Many agmatinases are known having such relatively high level of identity with the *E. coli* reference enzyme.

Further, in said embodiment, in particular all agmatine iminohydrolases and/or N-carbamoylputrescine amidohydrolases can be used in the process that have sufficient, i.e. at least 20%, more preferably at least 30%, and most preferably at least 40%, identity with the agmatine iminohydrolase and/or the N-carbamoylputrescine amidohydrolase from the *Pseudomonas* reference enzymes, and are capable of catalyzing the agmatine iminohydrolase, respectively the N-carbamoylputrescine amidohydrolase reaction. Many agmatine iminohydrolases and N-carbamoylputrescine amidohydrolases are known having such relatively high level of identity with the *Pseudomonas* reference enzymes.

The overexpressed arginine decarboxylase encoding gene in the above preferred embodiment of the invention is preferably an arginine decarboxylase gene speA originating from one of the genera selected from the group consisting of *Escherichia, Shigella, Salmonella, Yersinia, Pasteurella*, and *Neisseria*. More preferably, the overexpressed arginine decarboxylase encoding gene is preferably an arginine decarboxylase gene speA originating from one of the species selected from the group consisting of *Escherichia coli, Shigella flexneri, Salmonella enterica, Yersinia pestis, Pasteurella multocida*, and *Neisseria meningitides*.

In this preferred embodiment of the invention, moreover, the overexpressed agmatinase encoding gene preferably is an agmatinase gene speB originating from one of the genera selected from the group consisting of *Escherichia, Salmonella, Proteus, Photorhabdus, Vibrio*, and *Neisseria*. More preferably, the overexpressed agmatinase encoding gene is an agmatinase gene speB originating from one of the species selected from the group consisting of *Escherichia coli, Salmonella enterica, Proteus mirabilis, Photorhabdus luminescens, Vibrio cholerae*, and *Neisseria meningitidis*.

In this further preferred embodiment of the invention, further, the overexpressed agmatine iminohydrolase encoding gene and/or the overexpressed N-carbamoylputrescine amidohydrolase encoding gene is preferably an agmatine iminohydrolase gene aguA and/or an N-carbamoylputrescine amidohydrolase gene aguB originating from one of the genera selected from the group consisting of *Pseudomonas, Streptococcus, Streptomyces, Azotobacter, Arabidopsis, Novosphingobium*, and *Bacillus*. More preferably, the overexpressed agmatine iminohydrolase encoding gene and/or the overexpressed N-carbamoylputrescine amidohydrolase encoding gene is an agmatine iminohydrolase gene aguA and/or an N-carbamoylputrescine amidohydrolase gene aguB originating from one of the species selected from the group consisting of *Pseudomonas aeruginosa, Streptococcus mutans, Streptomyces avermitilis, Azotobacter vinelandii, Arabidopsis thaliana, Novosphingobium aromaticivorans*, and *Bacillus cereus*.

The process of the invention may be carried out in any suitable host organism. The hosts may be selected from the groups of production organisms (or cells) generally known to the skilled man in biosynthesis. Such organisms may be from eukaryotic origin, or—as is more preferred—from prokaryotic origin. Eukaryotic cells, for instance, can be cells from plants and fungi, and from various other groups, which other groups collectively are referred to as "Protista".

It is particularly preferred, that the process according to the invention is carried out in a host organism selected from the group consisting of *Saccharomyces* sp., *Bacillus* sp., *Corynebacterium* sp., *Escherichia* sp. and *Pichia* sp.

In the process of the invention, it is especially preferred that the microorganism to be used as a host is able to produce the amino acids ornithine and/or arginine. For most natural microorganisms this requirement is fulfilled because usually such capability is available in all wild type strains, since arginine represents an essential amino acid.

Of these species, *Escherichia* sp. are preferred because they are easy to handle by genetic manipulation in order to provide strains with the desired overexpressed enzyme activities. Moreover, *Escherichia* sp. already in nature contain almost each of the abovementioned enzyme activities (i.e. apart from the agu genes from plants), so that most of the overexpressed genes can be used as homologous genes. Also, *Corynebacterium* sp. (though lacking a natural ornithine decarboxylase) is particularly preferred because it is a suitable glutamate production strain that can be handled easily in fermentation processes.

In the process of the present invention glutamate is a very suitable precursor. Accordingly, the process is preferably being carried out in a host strain capable of formation of glutamate (for instance, *Corynebacterium glutamicum*).

Best results are being achieved when the process according to the invention is carried out in a host organism from the group consisting of *Saccharomyces cerevisiae, Corynebacterium* sp. and *Escherichia* sp. wherein, apart from the increased level of activity of an ornithine decarboxylase and of N-acetyl glutamate formation, at least also the level of activity of an arginine decarboxylase in combination with an agmatinase and/or an agmatine iminohydrolase and an N-carbamoylputrescine amidohydrolase enzyme is increased. As meant herein, for each of the enzymes mentioned the increased level of activity is compared with the native level of activity of the respective said enzyme activity in the host organism.

It will be clear that the process of the invention is preferably carried out under reaction conditions that are also usual as fermentation conditions. The process, therefore can be carried out batch-wise, but also—if so desired—fed-batch. It may be convenient to ensure that the organism used as host organism has, or is provided with, a suitable exporter system for the 1,4-diaminobutane formed: Preferably such exporter system is a native one.

The present invention, of course, finally also relates to all vectors, plasmids and hosts carrying an increased level of an ornithine decarboxylase activity (increased ODC activity) as compared to the native level of the ornithine decarboxylase activity, and an increased activity of N-acetylglutamate formation as compared to the native level of activity of N-acetylglutamate formation. In particular, for the preferred embodiments, the present invention also relates to all vectors, plasmids and hosts additionally carrying an increased level of activity of one or more of the other aforementioned enzyme activities according to the attached claims.

The invention will now be elucidated by means of some experimental results, which by no means are intended to limit the scope of the invention.

EXPERIMENTAL PART

General Procedures

Standard procedures were applied for all DNA manipulations (Sambrook, J. et al. (1989), *Molecular cloning: a laboratory manual*, 2nd Ed., Cold Spring Harbor Laboratory Press, Cold Spring Harbor, N.Y.). DNA was amplified from chromosomal DNA of *E. coli* LJ 110 (Zeppenfeld, et al., (2000), *J Bacteriol.* 182, 4443-4452), *Bacillus subtilis* ATCC10783, or *Corynebacterium glutamicum* ATCC13032 if not indicated otherwise. PCR amplification was performed using the proof-reading enzymes *SAWADY Pwo-DNA-Polymerase* (Peqlab Biotechnologie GmbH, Erlangen, Germany) or *Platinum Pfx DNA Polymerase* (Invitrogen, Karlsruhe, Germany) following the manufacture's protocol, whereas the verification of the constructed strains was carried out by colony PCR utilizing the Taq polymerase READYMIX (Sigma, Taufkirchen, Germany). Restriction sites for subsequent cloning as well as further mutations were introduced with oligonucleotides purchased from MWG-Biotech (Ebersberg, Germany). DNA fragments were purified with the MinElute Gel Extraction Kit (Qiagen, Hilden, Germany) following the manufacture's protocol. Preparation of Plasmid DNA was Accomplished by the Utilization of QIAprep Spin Miniprep Kit (Qiagen, Hilden, Germany). Verification of the constructed plasmids was carried out by restriction analysis and subsequent sequencing (Agowa, Berlin, Germany).

For high-level expression of genes, the vector pJF119EH (Fürste, J. P. et al. (1986), *Gene* 48, 119-131) was used suitable for IPTG-induced protein production based on the Isopropyl-beta-D-thiogalactopyranoside (IPTG) inducible tac promotor and the lac repressor system (lacI$^Q$).

Construction of Plasmids (i) Construction of the Plasmid pDAB2 (pJF119EH-speF)

The (inducible, biodegradative) ornithine decarboxylase encoding gene speF of *E. coli* LJ 110 (Zeppenfeld, et al., see general procedures) was cloned into the expression vector pJF119EH (Fürste, J. P. et al. (1986), *Gene* 48, 119-131). This vector allows a high-level protein production based on the transcriptional control of cloned genes under the isopropyl- β-D-thiogalactopyranoside (IPTG) inducible tac promotor and the lac repressor system (lacI$^Q$). For construction of the expression plasmid pDAB2 (pJF119EH-speF) the coding gene was cloned with original RBS (ribosomal binding site), start and stop codon.

The 2247 bp speF-containing DNA fragment was amplified from chromosomal DNA of E. coli LJ110 (accession number AE000172; nucleotides 10242-12468) using the following oligonucleotides:

[SEQ ID: No. 1]
5'-GAC CTG CTG*GTA* CCT AAA ATA AAG AGA TGA AA-3'

(mutations in bold, KpnI restriction site in italics) and

[SEQ ID: No. 2]
5'-TCG A*TC TAG* ACT GAC TCA TAA TTT TTC CC-3'

(mutations in bold, XbaI restriction site in italics).

The fragment was terminally modified with the restriction endonucleases KpnI and XbaI and ligated into the expression vector pJF119EH, which was cut in the same manner. After transformation in E. coli DH5α cells (Invitrogen, Karlsruhe, Germany), transformants were selected on LB agar plates containing 100 mg/l ampicillin. After preparation, the obtained plasmid pDAB2 (pJF119EH-speF, 7502 bp) was verified by restriction analysis and subsequent sequencing.

(ii) Construction of the Plasmid pDAB4 (PJF119EH-speC)

The (constitutive, biosynthetic) ornithine decarboxylase encoding gene spec of E. coli LJ 110 (Zeppenfeld, et al., see general procedures) was cloned into the expression vector pJF119EH (Fürste, J. P. et al. (1986), see (i)), allowing a strong gene expression based on the transcriptional control under the isopropyl-β-D-thiogalactopyranoside (IPTG) inducible tac promotor and the lac repressor system (lacI$^Q$). Therefore, the coding gene was cloned with original start and stop codon. Since, no conserved ribosomal binding site (RBS) could be determined for speC utilizing in silico studies, an optimized RBS was introduced 7 bp upstream of the spec start codon by mutagenesis.

The 2235 bp spec-containing DNA fragment was amplified from chromosomal DNA of E. coli LJ 110 (accession number AE000379; nucleotides 2650-4867) using the following oligonucleotides:

[SEQ ID: No. 3]
5'-GAG CTC TAG ACC AGT TTG AGG AAT ATC T-3'

(mutations in bold, XbaI restriction site in italics) and

[SEQ ID: No. 4]
5'-TTT T*GC ATG* CTT ACT TCA ACA CAT AAC CGT AC-3'

(mutations in bold, SphI restriction site in italics).

After terminal modification with the endonucleases XbaI and SphI, the PCR product was ligated into plasmid pJF119EH, which was cut in the same manner. After transformation in E. coli DH5a cells (Invitrogen, Karlsruhe, Germany), transformants were selected on LB agar plates containing 100 mg/l ampicillin. After preparation, the verification of the obtained plasmid pDAB4 (pJF119EH-speC, 7491 bp) was carried out by restriction analysis and subsequent sequencing.

(iii) Construction of the Plasmid pDAB1 (pJF119EH-argA)

The N-acetylglutamate synthase encoding gene argA of E. coli LJ 110 (Zeppenfeld, et al., see general procedures) was cloned into the expression vector pJF119EH (Fürste, J. P. et al. (1986), see (i)). The gene was cloned with original RBS (ribosomal binding site) and stop codon. However, the translation start was altered from GTG to ATG.

The 1365 bp argA-coding DNA fragment was amplified from chromosomal DNA of E. coli LJ110 (accession number AE000365; nucleotides 3312-4643) using the following oligonucleotides:

[SEQ ID: No. 5]
5'-ATA A*GA ATT* CAA AGA GGT GTG CCA TGG TAA AG-3'

(mutations in bold, EcoRI restriction site in italics) and

[SEQ ID: No. 6]
5'-TTT T*GG TAC* CTT ACC CTA AAT CCG CCA T-3'

(mutations in bold, KpnI restriction site in italics).

The fragment was terminally modified using the restriction endonucleases EcoRI and KpnI, and subsequently ligated into the expression plasmid pJF119EH, which was cut in the same manner. After transformation in E. coli DH5α cells (Invitrogen, Karlsruhe, Germany), transformants were selected on LB agar plates containing 100 mg/l ampicillin. After preparation, the verification of the obtained plasmid pDAB1 (pJF119EH-argA, 6627 bp) was carried out by restriction analysis and subsequent sequencing.

(iv) Construction of the Plasmid pDAB5 (pJF119EH-argA-speF)

In order to allow in-parallel production of the ornithine decarboxylase SpeF and the N-acetylglutamate synthase ArgA, the speF encoding gene of E. coli LJ110 (Zeppenfeld, et al., see general procedures) was cloned into the argA-expression vector pDAB1 (see (iii)).

The speF-containing DNA fragment (2225 bp) was cut out from the constructed plasmid pDAB2 (see A.1) by digestion with the endonucleases KpnI and XbaI and ligated into the argA containing plasmid pDAB1 (see (iii)), cut likewise. After transformation in E. coli DH5α cells (Invitrogen, Karlsruhe, Germany), transformants were selected on LB agar plates containing 100 mg/l ampicillin. After preparation, the obtained plasmid pDAB5 (pJF119EH-argA-speF, 8841 bp) for in-parallel SpeF and ArgA production was verified by restriction analysis.

(v) Construction of the Plasmid pDAB6 (pJF119EH-argA-speC)

In order to allow in-parallel production of the ornithine decarboxylase SpeC and the N-acetylglutamate synthase ArgA, the speC encoding gene of E coli LJ110 (Zeppenfeld, et al., see general procedures) was cloned into the argA-expression vector pDAB1 (see (iii)1).

By digestion of the constructed plasmid pDAB4 (see (ii)) with the endonucleotides XbaI and SphI, the 2225 bp DNA fragment containing the speC gene with optimized RBS was separated. Subsequently, the fragment was ligated into the argA-containing plasmid pDAB1 (see (i)), which was cut in the same manner. After transformation in E. coli DH5λ cells (Invitrogen, Karlsruhe, Germany), transformants were selected on LB agar plates containing 100 mg/l ampicillin. After preparation, the verification of the obtained plasmid pDAB6 (pJF119EH-argA-speC, 8830 bp) allowing the in-parallel expression of speC and argA was carried out by restriction analysis and subsequent sequencing.

(vi) Construction of the Plasmid pDAB7 (pJF119EH-speAB)

The arginine decarboxylase encoding gene speA as well as speB coding for the agmatinase of *E. coli* LJ110 (Zeppenfeld, et al., see general procedures) were cloned into the expression vector pJF119EH (Fürste, J. P. et al. (1986), see (i)). This way, the original operon structure of the genes as well as RBS, start and stop codon were maintained.

The 3079 bp speAB-containing DNA fragment was amplified from chromosomal DNA of *E. coli* LJ 10 (accession number AE000377; nucleotides 1190-4247) using the following oligonucleotides:

[SEQ ID: No. 7]
5'-ACA CTT *TCTAGA* ATA ATT TGA GGT TCG CTA TG-3'

(mutations in bold, XbaI restriction site in italics) and

5'-CAT GGC ATG CGG TGC TTA CTC G-3'  [SEQ ID: No. 8]

(mutations in bold, SphI restriction site in italics).

After terminal modification with the restriction endonucleases XbaI and SphI, the DNA fragment was ligated into the expression plasmid pJF119EH, which was cut likewise. After transformation in *E. coli* DH5α cells (Invitrogen, Karlsruhe, Germany), transformants were selected on LB agar plates containing 100 mg/l ampicillin. After preparation, the verification of the obtained plasmid pDAB7 (pJF119EH-speAB, 8339 bp) was carried out by restriction analysis and subsequent sequencing.

(vii) Construction of the Plasmid pDAB8 (pJF119EH-speF-speAB)

In order to allow in-parallel production of the ornithine decarboxylase SpeF, the arginine decarboxylase SpeA and the agmatinase SpeB, the speAB genes of *E. coli* LJ 10 (Zeppenfeld, et al., see general procedures) were cloned into the speF-expression vector pDAB2 (see (i)).

By digestion of the plasmid pDAB7 (see (vi)) with the restriction endonucleases XbaI and SphI, the 3067 bp comprising speAB gene-operon was separated and ligated into the speF containing plasmid pDAB2 (see (i)), which was cut in the same manner. After transformation in *E. coli* DH5α cells (Invitrogen, Karlsruhe, Germany), transformants were selected on LB agar plates containing 100 mg/l ampicillin. After preparation, the obtained plasmid pDAB8 (pJH119EH-speFAB, 10547 bp) allowing the in-parallel production of SpeFAB was verified by restriction analysis.

(viii) Construction of the Plasmid pDAB10 (pJF119EH-argA-speF-speAB)

In order to allow in-parallel production of the ornithine decarboxylase SpeF, the arginine decarboxylase SpeA, the agmatinase SpeB and the N-acetylglutamate synthase ArgA, the speAB genes of *E. coli* LJ110 (Zeppenfeld, et al., see general procedures) were cloned into the argA-speF-expression vector pDAB5 (see (iv)).

By digestion of the plasmid pDAB7 (see (vi)) with the restriction endonucleases XbaI and SphI, the 3067 bp comprising speAB gene-operon was separated and ligated into the argA-speF containing plasmid pDAB5 (see (iv)), which was cut in the same manner. After transformation in *E. coli* DH5α cells (Invitrogen, Karlsruhe, Germany), transformants were selected on LB agar plates containing 100 mg/l ampicillin.

After preparation, the obtained plasmid pDAB10 (pJH119EH-argA-speFAB, 11886 bp) allowing the in-parallel production of ArgA and SpeFAB was verified by restriction analysis.

(ix) Construction of the Plasmid pDAB37 (pJF119EH-argJBs-speF)

In order to allow in-parallel production of the ornithine decarboxylase SpeF and the $N^2$-acetyl-L-ornithine:L-glutamate N-acetyl transferase encoding gene ArgJ from *Bacillus subtilis* ATCC 10783, the argj encoding gene of *B. subtilis* was cloned into the speF-expression vector pDAB5 (see (iv)) by replacing the present argA gene. The gene was cloned with original RBS and stop codon.

The 1279 bp argj-containing DNA fragment was amplified from chromosomal DNA of *Bacillus subtilis* ATCC 10783 (accession number Z99109 (*B. subtilis* subsp. *subtilis* str. 168, complete genome (section 6 of 21)); nucleotides 184321-185600) using the following oligonucleotides:

[SEQ ID: No. 9]
5'-TCA CGC *GAATTC* ATC CAT AGA ACG GGA GAG-3'

(mutations in bold, EcoRI restriction site in italics) and

[SEQ ID: No. 10]
5'-CTT CAT TTC *GGTACC* CTT TAT TAC GTG CGA TAG CTC-3'

(mutations in bold, KpnI restriction site in italics). The oligonucleotides were constructed according to the sequence of argJ as present in the genome of the strain *B. subtilis* subsp. *subtilis* str. 168.

The amplified DNA-fragment and plasmid pDAB5 were restricted with the endonucleases EcoRI and KpnI. In case of pDAB5, two fragments of 1355 bp and 7486 bp were obtained. The 7486 bp fragment comprising vector pJF119EH and the gene speF was isolated and ligated with amplified DNA-fragment. After transformation in *E. coli* DH5a cells (Invitrogen, Karlsruhe, Germany), transformants were selected on LB agar plates containing 100 mg/l ampicillin. After preparation, the verification of the obtained plasmid pDAB37 (pJF119EH-argJBs-speC, 8749 bp) was carried out by restriction analysis and subsequent sequencing. Sequence analyses revealed, that the argJ gene cloned from *B. subtilis* ATCC 10783 differs from the argJ gene reported for *B. subtilis* subsp. *subtilis* str. 168. In comparison to protein ArgJ of *B. subtilis* subsp. *subtilis* str. 168 (accession number CAB12961) the protein ArgJ encoded from the argj gene present on plasmid pDAB37 shows the following exchanges: H72Q, P74A, T75A, L95I, F105L, G110D, H134Q, E142Q, A169T, R181A, T216I, A242G, D255E, N353H, I363L, A380D, D383E.

(x) Construction of the Plasmid pDAB38 (pJF119EH-argJCg-speF)

In order to allow in-parallel production of the ornithine decarboxylase SpeF and the $N^2$-acetyl-L-ornithine:L-glutamate N-acetyl transferase encoding gene ArgJ from *Corynebacterium glutamicum*, the argJ encoding gene of *C. glutamicum* ATCC 13032 was cloned into the speF-expression vector pDAB5 (see (iv)) by replacing the present argA gene. The gene was cloned with original RBS and stop codon.

The 1219 bp argj-containing DNA fragment was amplified from chromosomal DNA of *C. glutamicum* ATCC 13032

(accession number NC 006958 (*C. glutamicum* ATCC 13032, complete genome); nucleotides 1466650-1467869) using the following oligonucleotides:

[SEQ ID: No. 11]
5'-ACA CAT C*GA ATT* CAG TAG GAG TTC CAC ATG G-3'

(mutations in bold, EcoRI restriction site in italics)
and

[SEQ ID: No. 12]
5'-AGT GCT *GGT ACC* TTT TAA GAG CTG TAC GC 3'

(mutations in bold, KpnI restriction site in italics).

The amplified DNA-fragment and plasmid pDAB5 were restricted with the endonucleases EcoRI and KpnI. In case of pDAB5, two fragments of 1355 bp and 7486 bp were obtained. The 7486 bp fragment comprising vector pJF119EH and the gene speF was isolated and ligated with the amplified DNA-fragment. After transformation in *E. coli* DH5α cells (Invitrogen, Karlsruhe, Germany), transformants were selected on LB agar plates containing 100 mg/l ampicillin. After preparation, the verification of the obtained plasmid pDAB38 (pJF119EH-argJCg-speF, 8679 bp) was carried out by restriction analysis and subsequent sequencing.

(xi) Construction of the Plasmid pDAB3 (pJF119EH-SPeC-nRBS)

The (constitutive, biosynthetic) ornithine decarboxylase encoding gene speC of *E coli* LJ110 (Zeppenfeld, et al., see general procedures) was cloned into the expression vector pJF119EH (Fürste, J. P. et al. (1986), Gene 48, 119-131), allowing a strong gene expression based on the transcriptional control under the isopropyl-β-D-thiogalactopyranoside (IPTG) inducible tac promotor and the lac repressor system (lacI$^Q$). Therefore, the coding gene speC was cloned with original RBS, start and stop codon.

The 2235 bp speC$_{nRBS}$-containing DNA fragment was amplified from chromosomal DNA of *E coli* LJ 110 (accession number AE000379; nucleotides 2650-4867) using the following oligonucleotides:

[SEQ ID: No. 13]
5'-GAG *CTC TAG* ACC AGT TTG ACC CAT ATC T-3'

(mutations in bold, XbaI restriction site in italics)
and

[SEQ ID: No. 14]
5'-TTT *TGC ATG* CTT ACT TCA ACA CAT AAC CGT AC-3'

(mutations in bold, SphI restriction site in italics).

After terminal modification with the endonucleases XbaI and SphI, the PCR product was ligated into plasmid pJF119EH, which was cut in the same manner.

After transformation in *E. coli* DH5α cells (Invitrogen, Karlsruhe, Germany), transformants were selected on LB agar plates containing 100 mg/l ampicillin. After preparation, the verification of the obtained plasmid pDAB3 (pJF119EH-speC$_{nRBS}$, 7491 bp) was carried out by restriction analysis and subsequent sequencing.

Comparative Experiment A

Production of 1,4-butanediamine Via the Sole Overexpression of Ornithine Decarboxylase speC, with Gene Expression Induced by IPTG (Shake Flask)

The influence of overexpression of ornithine decarboxylase encoding gene spec on DAB production was investigated within the *E. coli* host strain LJ 110 (Zeppenfeld, et al., see general procedures) carrying the plasmid pDAB3 (see (ix)).

This strain was tested in shake flask experiments utilizing minimal salt medium consisting of $MgSO_4 \cdot 7H_2O$ (300 mg/l), $CaCl_2 \cdot 2H_2O$ (15 mg/l), $KH_2PO_4$ (3 g/l), $K_2HPO_4$ (12 g/l), NaCl (100 mg/l), $(NH_4)_2SO_4$ (5 g/l), Na citrate-$3H_2O$ (1 g/l), $FeSO_4 \cdot 7H_2O$ (75 mg/l), thiamine-HCl (vitamin B1) (5 mg/l) as well as the trace elements $Al_2(SO_4)_3 \cdot 18H_2O$ (3 mg/l), $CoCl_2 \cdot 6H_2O$ (1.05 mg/l), $CuSO_4 \cdot 5H_2O$ (3.75 mg/l), $H_3BO_3$ (0.75 mg/l), $MnCl_2 \cdot 4H_2O$ (30 mg/l), $Na_2MoO_4 \cdot 2H_2O$ (4.5 mg/l), $NiSO_4 \cdot 6H_2O$ (3 mg/l) and $ZnSO_4 \cdot 7H_2O$ (22.5 mg/l). A stock solution of glucose (500 g/l) was autoclaved separately and added to the sterilized medium up to a final concentration of 10 g/l.

A preculture of minimal salt medium containing 100 mg/l ampicilline was inoculated with 1-5 µl/ml stock solution and incubated at 33° C., 180 rpm for 16 h up to an $OD_{620}$ of 2.5 ml of this culture was subsequently used for inoculation of the main culture consisting of 50 ml of the same medium, which was incubated for 24 h at 33° C. and 180 rpm. Since the cells reached an $OD_{620nm}$ of 1.5 (after ~7 h), gene expression was induced by the addition of 10 µM IPTG.

In order to observe the time-dependent DAB production, samples were taken at different time points during cultivation. After separation of the cells utilizing centrifugation, diluted supernatant was analyzed by HPLC. Here, the contained amines were detected as ortho-phthaldialdehyde (OPA) derivatives at 230 nm on a Hewlett-Packard 1100 Series instrument, using a $C_{18}$-reverse phase column (Nucleosil 120-5 $C_{18}$, Macherey & Nagel, Duren, Germany) equilibrated to 50% buffer B (buffer A, 0.1 M sodium acetate pH 7.2; buffer B methanol). For separation, the following gradient was applied: 1-7 min linear gradient from 50% to 75% buffer B with a flow rate of 0.5 ml/min, 7-13 min 75% to 85% buffer B with a flow rate of 0.5 ml/min, 13-14.5 min 85% to 50% buffer B with a low rate of 1 ml/min, 14.5-17 min 50% buffer B with a flow rate of 1 ml/min and 17-20 min at 50% buffer B with a flow rate of 0.5 ml/min.

By the utilization of standard substances for calibration, the following DAB concentrations could be determined (see Table 1) and verified by NMR spectroscopy.

TABLE 1

DAB formation utilizing ODC overproduction in *E. coli*

| Strain used | Gene expressed | DAB concentration [mg/l] |
| --- | --- | --- |
| LJ110 pDAB3 | speC | 50 |

Examples
Improvement of 1,4-Butanediamine Production by Increased Ornithine Decarboxylation Activity Combined with Increased N-acetylglutamate Formation Activity Example 1

Production of 1,4-butanediamine Utilizing ODC as Well as ArgA Overproduction (Shake Flask)

The influence of the in-parallel production of N-acetylglutamate synthase ArgA, catalyzing the first step in ornithine biosynthesis starting from glutamate, and ornithine decarboxylases SpeF or SpeC on DAB production was investigated within the *E. coli* host strain LJ110 (Zeppenfeld, et al., see general procedures) carrying the plasmid pDAB5 (see (iv)) or pDAB6 (see (v)).

These strains were tested in shake flask experiments in minimal salt medium (see Comparative Experiment A). Therefore, a preculture of minimal salt medium containing 100 mg/l ampicilline was inoculated with 1-5 µl/ml stock solution and incubated at 33° C., 180 rpm for 16 h up to an optical density at 620 nm of 2. 5 ml of this culture was subsequently used for inoculation of the main culture consisting of 50 ml of the same medium, which was incubated for 24 h at 33° C. and 180 rpm. Since the cells reached an $OD_{620nm}$ of 1.5 (after ~7 h), gene expression was induced by the addition of 10 µM IPTG.

In order to observe the time-dependent DAB production, samples were taken at different time points during cultivation. After separation of the cells utilizing centrifugation, the supernatant was analyzed by HPLC (see Comparative Experiment A). By the utilization of standard substances for calibration, the following DAB concentrations could be determined (see Table 2).

TABLE 2

DAB formation utilizing in-parallel ArgA and ODC overproduction in *E. coli*

| Used strain | expressed genes | DAB concentration [mg/l] |
|---|---|---|
| LJ110 pDAB5 | argA speF | 893 |
| LJ110 pDAB6 | argA speC | 1064 |

Example 2

Production of 1,4-butanediamine Utilizing ODC as Well as ArgJ Overproduction (Shake Flask)

The influence of the in-parallel production of the $N^2$-acetyl-L-ornithine:L-glutamate N-acetyl transferase encoding gene ArgJ either from *C. glutamicum* or *B. subtilis*, catalyzing the formation of N-acetylglutamate and ornithine from L-glutamate and N-acetylornithine, and ornithine decarboxylases SpeF or SpeC on DAB production was investigated within the *E. coli* host strain LJ110 (Zeppenfeld, et al., see general procedures) carrying the plasmid pDAB37 (see (ix)) or pDAB38 (see (x)).

These strains were tested in shake flask experiments in minimal salt medium (see Comparative Experiment A). Therefore, a preculture of minimal salt medium containing 100 mg/l ampicilline was inoculated with 1-5 µl/ml stock solution and incubated at 33° C., 180 rpm for 16 h up to an optical density at 620 nm of 2. 5 ml of this culture was subsequently used for inoculation of the main culture consisting of 50 ml of the same medium, which was incubated for 24 h at 33° C. and 180 rpm. Since the cells reached an $OD_{620nm}$ of 1.5 (after ~7 h), gene expression was induced by the addition of 50 µM IPTG.

In order to observe the time-dependent DAB production, samples were taken at different time points during cultivation. After separation of the cells utilizing centrifugation, the supernatant was analyzed by NMR. A sample of the culture supernatant was adjusted to pH 5.8, lyophilized, and redissolved in $D_2O$.600 MHz $^1$H-NMR at 323 K showed the expected resonance spectrum and spiking with a small amount of DAB confirmed the presence of DAB. By the utilization of standard substances for calibration, the following DAB concentrations could be determined (see Table 3).

TABLE 3

DAB formation utilizing in-parallel ArgJ and ODC overproduction in *E. coli*

| Used strain | expressed genes | DAB concentration [mg/l] |
|---|---|---|
| LJ110 pDAB37 | argJBs speF | 1050 |
| LJ110 pDAB38 | argJCg speF | 1130 |

Example 3

Improvement of 1,4-butanediame Production within Batch Starting from Ornithine as Well as Arginine (Shake Flask)

For demonstrating further improvement of DAB formation starting from ornithine as well as arginine, the influence of combined overproduction of the ornithine decarboxylase SpeF, the arginine decarboxylase SpeA and the agmatinase SpeB was investigated. In addition, in order to ensure a proper precursor supply, these investigations were combined in a further experiment with the overproduction of the N-acetylglutamate synthase ArgA, catalyzing the first step in ornithine biosynthesis starting from glutamate.

Therefore, shake flask cultivations were carried out in minimal salt medium (see A.3) by the utilization of the *E coli* host strain LJ110 (Zeppenfeld, et al., see general procedures) carrying the plasmids pDAB8 and pDAB10, respectively (see 2.2 and 2.3). Therefore, a preculture of minimal salt medium containing 100 mg/l ampicilline was inoculated with 1-5 µl/ml stock solution and incubated at 33° C., 180 rpm for 16 h up to an optical density at 620 nm of 2. 5 ml of this culture was subsequently used for inoculation of the main culture consisting of 50 ml of the same medium, which was incubated for 24 h at 33° C. and 180 rpm. Since the cells reached an $OD_{620nm}$ of 1.5 (after ~7 h), gene expression was induced by the addition of 10 µM IPTG.

In order to observe the time-dependent DAB production, samples were taken at different time points during cultivation. After separation of the cells utilizing centrifugation, the supernatant was analyzed by HPLC (see Comparative Experiment A). By the utilization of standard substances for calibration, the following DAB concentrations could be determined (see Table 4).

TABLE 4

DAB formation starting from ornithine as well as arginine in *E. coli*

| Used strain | expressed gene | DAB concentration [mg/l] |
|---|---|---|
| LJ110 pDAB8 | speFAB | 1025 |
| LJ110 pDAB10 | argA speFAB | 1433 |

The invention claimed is:

1. Process for biochemical synthesis of 1,4-butanediamine in a microorganism having an increased level of ornithine decarboxylase (ODC) activity as compared to the native level of ornithine decarboxylase activity, wherein there is increased N-acetylglutamate formation in said microorganism as compared to the native level of N-acetylglutamate formation; the process comprising:
  (a) culturing said microorganism to excrete 1,4-butanediamine into a fermentation broth, whereby said increased ODC activity is achieved by overexpression of an ornithine decarboxylase encoding gene speF or speC, each belonging to E.C.4.1.1.17, and the increased activity of N-acetylglutamate formation is achieved by overexpression of at least one of an N-acetyleglutamate synthase encoding argA (belonging to E.C.2.3.1.1) and an $N^2$-acetyl-L-ornithine:L-gluamate N-acetyl transferase encoding gene argJ (belonging to E.C.2.3.1.35), and
  (b) recovering said 1,4-butanediamine from the fermentation broth.

2. Process according to claim 1, wherein the ornithine decarboxylase encoding gene speF or speC originate from one of the genera selected from the group consisting of *Escherichia, Shigella, Salmonella, Yersinia*, and *Shewanella*.

3. Process according to claim 2, wherein the ornithine decarboxylase encoding gene is originating from one of the species selected from the group consisting of *Escherichia coli, Shigella flexneri, Salmonella typhimutium, Yersinia pestis*, and *Shewanella oneidensis*.

4. Process according to claim 1, wherein the ornithine decarboxylase encoding gene is speF originating from one of the species selected from the group consisting of *Escherichia coli, Salmonella typhimutium*, and *Shewanella oneidensis*.

5. Process according to claim 1, wherein the increased activity of N-acetylglutamate formation is achieved by overexpression of an N-acetylglutamate synthase encoding gene argA originating from one of the genera selected from the group consisting of *Escherichia, Shigella, Salmonella, Yersinia, Photorhabdus*, and *Buchnera*.

6. Process according to claim 5, wherein the increased activity of N-acetylglutamate formation is achieved by overexpression of an N-acetylglutamate synthase encoding gene argA originating from one of the species selected from the group consisting of *Escherichia coli, Shigella flexneri, Salmonella enterica, Yersinia pestis, Photorhabdus luminescens*, and *Buchnera aphidicola*.

7. Process according to claim 1, wherein the increased activity of N-acetylglutamate formation is achieved by overexpression of an $N^2$-acetyl-L-ornithine:L-glutamate N-acetyl transferase encoding gene argJ (gene encoding an enzyme classified (E.C.) in group E.G. 2.3.1.35) originating from one of the genera selected from the group consisting of *Bacillus, Listeria, Oceanobacillus, Staphylococcus, Lactobacillus, Corynebacterium, Mycobacterium, Thermobifida, Streptomyces*, and *Bifidobacterium*.

8. Process according to claim 7, wherein the increased activity of N-acetylglutamate formation is achieved by overexpression of an $N^2$-acetyl-L-ornithine: L-glutamate N-acetyl transferase encoding gene originating from one of the species selected from the group consisting of *Bacillus cereus, Listeria monocytogenes, Oceanobacillus iheyensis, Staphylococcus epidermis, Lactobacillus plantarum, Lactobacillus lactis, Corynebacterium glutamicum, Mycobacterium leprae, Thermobifida fusca, Streptomyces coelicor*, and *Bifidobacterium longum*.

9. Process according to claim 1, wherein additionally also an increased enzyme activity is obtained for at least two other enzymes by overexpression of either
  (i) an arginine decarboxylase encoding gene speA (gene encoding an enzyme classified (E.C.) in group E.C. 4.1.1.19) and an agmatinase encoding gene speB (belonging to E.C. 3.5.3.11; also referred to as agmatine ureahydrolase encoding gene); or
  (ii) an arginine decarboxylase encoding gene speA (gene encoding an enzyme classified (E.C.) in group E.C. 4.1.1.19), and an agmatine iminohydrolase encoding gene aguA (belonging to E.C. 3.5.3.12; also referred to as agmatine deiminase encoding gene), and an N-carbamoylputrescine amidohydrolase encoding gene aguB (gene encoding an enzyme classified (E.C.) in group E.C. 3.5.1.53), and optionally also an agmatinase encoding gene speB (gene encoding an enzyme classified (E.C.) in group E.C. 3.5.3.11).

10. Process according to claim 9, wherein the overexpressed arginine decarboxylase encoding gene is an arginine decarboxylase gene speA originating from one of the genera selected from the group consisting of *Escherichia, Shigella, Salmonella, Yersinia, Pasteurella*, and *Neisseria*.

11. Process according to claim 10, wherein the overexpressed arginine decarboxylase encoding gene is an arginine decarboxylase gene speA originating from one of the species selected from the group consisting of *Escherichia coli, Shigella flexneri, Salmonella enterica, Yersinia pestis, Pasteurella multocida*, and *Neisseria meningitidis*.

12. Process according to claim 9, wherein the overexpressed agmatinase encoding gene is an agmatinase gene speB originating from one of the genera selected from the group consisting of *Escherichia, Salmonella, Proteus, Photorhabdus, Vibrio*, and *Neisseria*.

13. Process according to claim 12, wherein the overexpressed agmatinase encoding gene is an agmatinase gene speB originating from one of the species selected from the group consisting of *Escherichia coli, Salmonella enterica, Proteus mirabilis, Photorhabdus luminescens, Vibrio cholerae*, and *Neisseria meningitidis*.

14. Process according to claim 9, wherein the overexpressed agmatine iminohydrolase encoding gene and/or the overexpressed N-carbamoylputrescine amidohydrolase encoding gene is an agmatine iminohydrolase gene aguA and/or an N-carbamoylputrescine amidohydrolase gene aguB originating from one of the genera selected from the group consisting of *Pseudomonas, Streptococcus, Streptomyces, Azotobacter, Arabidopsis, Novosphingobium,* and *Bacillus.*

15. Process according to claim 14, wherein the overexpressed agmatine iminohydrolase encoding gene and/or the overexpressed N-carbamoylputrescine amidohydrolase encoding gene is an agmatine iminohydrolase gene aguA and/or an N-carbamoylputrescine amidohydrolase gene aguB originating from one of the species selected from the group consisting of *Pseudomonas aeruginosa, Streptococcus mutans, Streptomyces avermitilis, Azotobacter vinelandii, Arabidopsis thaliana, Novosphingobium aromaticivorans,* and *Bacillus cereus.*

16. Process according to claim 1, wherein the process is carried out in a host organism selected from the group consisting of *Saccharomyces* sp., *Bacillus* sp., *Corynebacterium* sp., *Escherichia* sp., and *Pichia* sp.

17. Process according to claim 1, wherein the process is carried out in a host organism selected from the group of *Saccharomyces cerevisiae, Corynebacterium* sp., and *Escherichia* sp. and in that, apart from the increased level of activity of an ornithine decarboxylase and of N-acetylglutamate formation, at least also the level of activity of an arginine decarboxylase in combination with an agmatinase and/or an agmatine iminohydrolase and an N-carbamoylputrescine amidohydrolase is increased.

18. An isolated microorganism having an increased level of ornithine decarboxylase (ODC) activity as compared to the native level of ornithine decarboxylase activity and an increased activity of N-acetylglutamate formation as compared to the native level of activity of N-acetylglutamate formation, whereby said increased ODC activity is achieved by overexpression of an ornithine decarboxylase encoding gene speF or speC, each belonging to E.C.4.1.1.17, and the increased activity of N-acetylglutamate formation is achieved by overexpression of at least one of an N-acetyleglutamate synthase encoding argA (belonging to E.C.2.3.1.1) and an $N^2$-acetyl-L-ornithine: L-gluamate N-acetyl transferase encoding gene argJ (belonging to E.C.2.3.1.35).

19. Microorganism according to claim 18, wherein there is an increased level of activity of one or more further enzyme activities selected from the group consisting of arginine decarboxylase, agmatinase, agmatine iminohydrolase, and N-carbamoylputrescine amidohydrolase.

* * * * *

SEQUENCE LISTING

<160> NUMBER OF SEQ ID NOS: 14

<210> SEQ ID NO 1
<211> LENGTH: 32
<212> TYPE: DNA
<213> ORGANISM: Artificial Sequence
<220> FEATURE:
<223> OTHER INFORMATION: primer

<400> SEQUENCE: 1
gacctgctgg tacctaaaat aaagagatga aa         32

<210> SEQ ID NO 2
<211> LENGTH: 30
<212> TYPE: DNA
<213> ORGANISM: Artificial Sequence
<220> FEATURE:
<223> OTHER INFORMATION: primer

<400> SEQUENCE: 2
tcgatctaga ctgactcata atttttcccc            30

<210> SEQ ID NO 3
<211> LENGTH: 28
<212> TYPE: DNA
<213> ORGANISM: Artificial Sequence
<220> FEATURE:
<223> OTHER INFORMATION: primer

<400> SEQUENCE: 3
gagctctaga ccagtttgag gaatatct              28

<210> SEQ ID NO 4
<211> LENGTH: 32
<212> TYPE: DNA
<213> ORGANISM: Artificial Sequence
<220> FEATURE:
<223> OTHER INFORMATION: primer

<400> SEQUENCE: 4
ttttgcatgc ttacttcaac acataaccgt ac         32

<210> SEQ ID NO 5
<211> LENGTH: 32
<212> TYPE: DNA
<213> ORGANISM: Artificial Sequence
<220> FEATURE:
<223> OTHER INFORMATION: primer

<400> SEQUENCE: 5
ataagaattc aaagaggtgt gccatggtaa ag         32

<210> SEQ ID NO 6
<211> LENGTH: 28
<212> TYPE: DNA
<213> ORGANISM: Artificial Sequence
<220> FEATURE:
<223> OTHER INFORMATION: primer

<400> SEQUENCE: 6
ttttggtacc ttaccctaaa tccgccat               28

<210> SEQ ID NO 7
<211> LENGTH: 32
<212> TYPE: DNA

```
<213> ORGANISM: Artificial Sequence
<220> FEATURE:
<223> OTHER INFORMATION: primer

<400> SEQUENCE: 7
acactttcta gaataatttg aggttcgcta tg                                    32

<210> SEQ ID NO 8
<211> LENGTH: 22
<212> TYPE: DNA
<213> ORGANISM: Artificial Sequence
<220> FEATURE:
<223> OTHER INFORMATION: primer

<400> SEQUENCE: 8
catggcatgc ggtgcttact cg                                               22

<210> SEQ ID NO 9
<211> LENGTH: 30
<212> TYPE: DNA
<213> ORGANISM: Artificial Sequence
<220> FEATURE:
<223> OTHER INFORMATION: primer

<400> SEQUENCE: 9
tcacgcgaat tcatccatag aacgggagag                                       30

<210> SEQ ID NO 10
<211> LENGTH: 36
<212> TYPE: DNA
<213> ORGANISM: Artificial Sequence
<220> FEATURE:
<223> OTHER INFORMATION: primer

<400> SEQUENCE: 10
cttcatttcg gtacccttta ttacgtgcga tagctc                                36

<210> SEQ ID NO 11
<211> LENGTH: 31
<212> TYPE: DNA
<213> ORGANISM: Artificial Sequence
<220> FEATURE:
<223> OTHER INFORMATION: primer

<400> SEQUENCE: 11
acacatcgaa ttcagtagga gttccacatg g                                     31

<210> SEQ ID NO 12
<211> LENGTH: 29
<212> TYPE: DNA
<213> ORGANISM: Artificial Sequence
<220> FEATURE:
<223> OTHER INFORMATION: primer

<400> SEQUENCE: 12
agtgctggta cctttttaaga gctgtacgc                                       29

<210> SEQ ID NO 13
<211> LENGTH: 28
<212> TYPE: DNA
<213> ORGANISM: Artificial Sequence
<220> FEATURE:
<223> OTHER INFORMATION: primer

<400> SEQUENCE: 13
gagctctaga ccagtttgac ccatatct                                         28
```

```
<210> SEQ ID NO 14
<211> LENGTH: 32
<212> TYPE: DNA
<213> ORGANISM: Artificial Sequence
<220> FEATURE:
<223> OTHER INFORMATION: primer

<400> SEQUENCE: 14
ttttgcatgc ttacttcaac acataaccgt ac                                       32
```